United States Patent [19]

Unterleitner

[11] Patent Number: 4,498,766
[45] Date of Patent: Feb. 12, 1985

[54] LIGHT BEAM FOCAL SPOT ELONGATION IN FLOW CYTOMETRY DEVICES

[75] Inventor: Fred C. Unterleitner, Palo Alto, Calif.

[73] Assignee: Becton, Dickinson and Company, Paramus, N.J.

[21] Appl. No.: 361,672

[22] Filed: Mar. 25, 1982

[51] Int. Cl.³ .............................................. G01N 21/64
[52] U.S. Cl. ...................................... 356/73; 356/318; 250/461.2
[58] Field of Search .................... 356/72, 73, 317, 318, 356/337–343; 250/458.1, 459.1, 461.1, 461.2

[56] References Cited

U.S. PATENT DOCUMENTS 3,606,547  9/1971  Iwahashi .............................. 356/325
3,710,933  1/1973  Fulwyler et al. ........................ 209/3
3,826,364  7/1974  Bonner et al. ........................... 209/3
4,243,318  1/1981  Stohr ................................. 356/318 X
4,293,221  10/1981  Kay et al. ............................. 356/318

Primary Examiner—Vincent P. McGraw
Attorney, Agent, or Firm—Richard J. Rodrick

[57] ABSTRACT

A flow cytometry apparatus comprises a nozzle for flowing particles in a stream of fluid. A source of light, such as from a laser, is adapted to direct a beam of light at the flowing particles. A beam focusing lens is positioned in the optical path of the light beam to provide an elliptical beam spot at the focal stream to thereby elongate the focal spot of the beam. One or more parameters of the particles in the stream related to light from the beam striking the particles is detected in the flow cytometry apparatus.

12 Claims, 2 Drawing Figures

LIGHT BEAM FOCAL SPOT ELONGATION IN FLOW CYTOMETRY DEVICES

BACKGROUND OF THE INVENTION

1. Field of the Invention

The present invention relates to flow cytometry apparatus, and more particularly, concerns an apparatus for detecting light parameters of particles flowing in a continuous stream, such apparatus utilizing a laser or other light source to direct a beam of light at the flowing particles.

2. Description of the Prior Art

Flow analysis of particles has been employed in the determination of various characteristics of individual particles. Flow cytometry devices have long been utilized for this purpose. In the broadest sense, a flow cytometry device as used and meant herein is a device which detects cells or particles as they flow, preferably individually, through an orifice. In addition to the capability of detecting particles flowing in a continuous stream, flow cytometry devices have been devised to determine volume, size, and other parameters of the flowing particles, particularly as such parameters are related to a source of light directed at them when flowing through the orifice.

In particular, many flow cytometry devices, including cell analyzers and cell sorters, rely upon a source of light energy directed against the flowing particles to thereafter establish certain measurements associated with the light which strikes the particles. For example, a device described in U.S. Pat. No. 3,710,933 measures cell volume through a Coulter-type orifice, and then measures light scatter and fluorescence of the particles that are being evaluated. In U.S. Pat. No. 3,826,364, an apparatus is disclosed which physically separates particles such as functionally different cell types. In this patented cell sorter, a laser provides illumination which is focused on the stream of particles by a suitable lens or lens system so that there is highly localized scatter from particles therein. In addition, a high intensity source of illumination is directed onto the stream of particles for the excitation of fluorescent particles contained therein. Luminescence from the excited fluorescent particles is then detected by suitable detection equipment. Certain fluorescent particles may be selectively charged and then separated by deflecting them into specific receptacles.

When utilizing lasers or other coherent light sources for illumination in flow cytometry device, obtaining optimum fluorescent pulse height resolution involves a balance between illumination uniformity, which determines the uniformity of fluorescence with particle position, and laser beam intensity which determines the available fluorescence photon flux. In presently known flow cytometry devices utilizing a laser for illumination, the laser beam focal waist is very narrow and thereby significantly affects sensitivity of the fluorescence signal. In circumstances where the fluorescence emitted from particles is weak, it is desired to have increased capability so that these weak fluorescent signals may be monitored. Accordingly, in the balance between illumination uniformity and laser beam intensity, as mentioned above, it remains a desirable feature to be able to improve the fluorescence sensitivity in the flow cytometry device.

SUMMARY OF THE INVENTION

The flow cytometry apparatus of the present invention comprises means for flowing particles in a stream of fluid. A source of coherent light is adapted to direct a beam of light at the flowing particles. Beam focusing lens means is positioned in the optical path of the light beam to provide an elliptical beam spot at the fluid stream to thereby elongate the focal spot of the beam. Means is provided for detecting one or more parameters of the particles in the stream related to light from the beam striking the particles.

In a preferred embodiment of the present invention, the apparatus detects light parameters of particles flowing in a continuous stream. A nozzle produces a stream of flowing particles in a continuous stream. A laser is adapted to direct a beam of light at a pre-selected wavelength of light. A beam focusing lens is adjustably positioned in the optical path of the laser beam. This lens is preferably positioned at an adjustable angle which can be varied around a vertical axis through its optical center. The lens is adapted to focus the laser beam onto the fluid stream. A light detector detects light from the laser beam scattered by striking particles in the fluid stream. Preferably, a fluorescence detector is provided for detecting fluorescence generated by the particles as a result of the laser beam striking same. In this preferred embodiment of the present invention, the lens lies at an angle, and can be varied around its vertical axis.

In accordance with the principles of the present invention, improved sensitivity of fluorescence is achieved by optimizing the optical elements of a flow cytometry device. By tilting the focusing lens at an angle relative to the laser, or other light, beam axis, the light beam focal waist becomes elongated. The focal spot at the stream of flowing particles therefore becomes elliptical as a result of the astigmatism introduced into the light beam by tilting the focus lens at an angle. This elliptical focal spot allows the light energy from the laser to be focused into a focal spot wherein the energy distribution in the direction of particle travel is optimized thereby affecting fluorescence sensitivity. In addition, and due to the width of the beam spot in the horizontal plane, sensitivity to particle stream flow rate, i.e., stream diameter, is reduced. As a result of the features of the present invention optimization of measurement of almost identically stained fluorescent particles may be made. In addition, the present invention allows different ellipticity to be introduced into the beam spot merely by varying the angle of tilt of the lens about its optical center. This therefore provides variable width focal spot at almost constant minor spot diameter readily achieved by tilting the lens axis slightly with respect to the laser beam axis whereby astigmatism is introduced. Moreover, the optical elements of the present invention are adaptable to presently known and available flow cytometry devices. The present invention clearly permits optimization of the focal spot intensity (optimum photon statistics) and uniformity (flow stability requirement) to achieve best photocurrent pulse uniformity from identically stained samples or resolution of slightly differently stained subpopulations of samples. The adjustable lens angle contributes to this optimization feature since the optimum focal spot will vary with available light power and with the amount of stain per sample particle.

DETAILED DESCRIPTION

Figure 1:
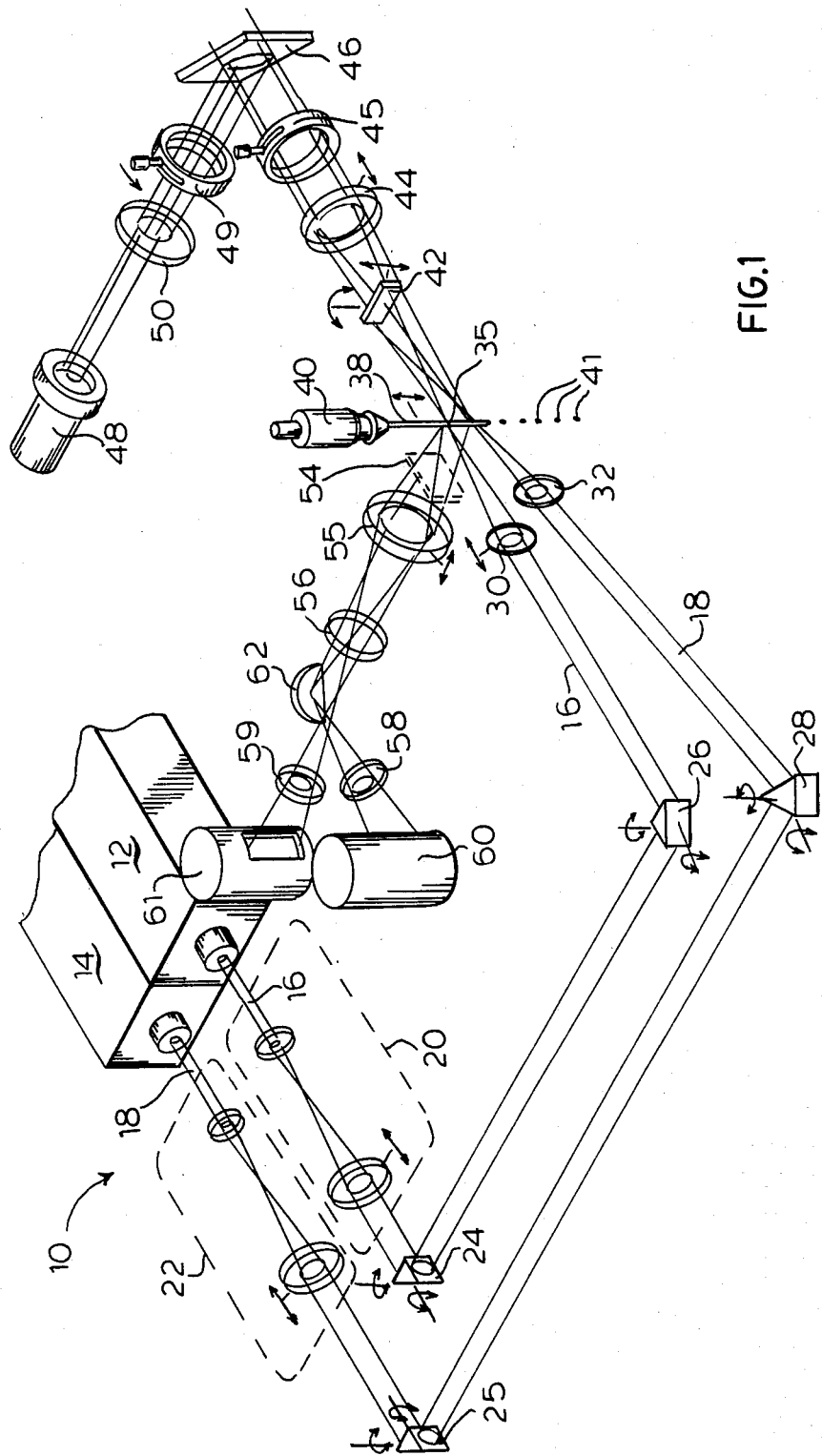
FIG. 1 is a schematic illustration of a preferred embodiment of the optical elements and light paths of a flow cytometry device particularly useful for determining fluorescence and light scatter parameters of particles flowing in a fluid stream.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting to the drawings, and FIG. 1 in particular, the optical and particle flow elements of a flow cytometry device 10 are illustrated. The optical and flow elements of FIG. 1 instrument known as the FACS FLUORESCENCE-ACTIVATED CELL SORTER, manufactured and sold by the FACS Systems Division of Becton, Dickinson and Company, Sunnyvale, Calif. The FACS cell sorter analyzes and separates cell populations on the basis of light scatter and fluorescence in a wide variety of research laboratory applications. In addition to the optical and flow elements to be described in more particular detail herein, and which may be embodied in an instrument such as the FACS cell sorter, other details of a cell sorting apparatus useful in conjunction with the present invention are described in U.S. Pat. No. 3,826,364. The optical elements, in particular, of the present invention represent the essence of the improvement in flow cytometry devices such as described in the aforementioned patent.

As illustrated in FIG. 1, illuminating light is provided for the present flow cytometry device by two lasers 12 and 14. In this embodiment being described, two sources of light are provided in flow cytometry device 10 so that it is possible to detect and monitor two different types of particles having different fluorescence characteristics. It is understood, however, that the inclusion of two lasers in this embodiment being described is merely preferable and serves as an exemplary embodiment of employing more than one fluorescence channel and analysis elements in the type of invention being described. Moreover, the elements of the present invention may be utilized just as satisfactorily if only one laser is employed in the flow cytometry apparatus. Similarly, more than two lasers may be utilized, if feasible and practicable.

In the present invention, lasers 12 and 14 are preferably high powered, argon-ion lasers, having primary emissions at specific wavelengths. For example, laser 12 is preferably selected to operate in the ultraviolet region whereby fluorochromes on particles passing through the light generated by laser 12 will become excited. Laser 14 is preferably selected to operate at a different wavelength than laser 12. This permits double tagging particular cells or particles with different fluorochromes and measuring the uptake for each, thereby providing simultaneous measurement of two cell or particle properties, as described more completely hereinafter. It is appreciated that while lasers, which generate a source of coherent light, are preferred for purposes of the present invention, other light generating sources, including those which generate incoherent light, fall within the purview of the present invention.

Emerging from lasers 12 and 14 each beam 16 and 18, respectively, has a diameter of approximately 1.6 mm. The beams pass through beam expanders schematically indicated by numerals 20 and 22 which enlarge each beam to a diameter of approximately 6 mm while retaining its parallel character. The beam expanders may be adjusted for ultraviolet operation or for other visible line operation. As each beam emerges from the beam expander, each 6 mm beam enters the front face of a total internal reflection prism 24 and 25, respectively, which reflects the beam by an angle of ninety degrees. These prisms are preferably fabricated of coated fused silica to provide maximum transmission. Various adjustment mechanisms may be provided to rotate the prisms in the vertical and the horizontal plane to align and direct the beams. Thereafter, the beams strike second total internal reflection prisms 26 and 28 which direct the beams toward the final focusing lenses. Once again, prisms 26 and 28 may be adjustable in the horizontal and the vertical planes for proper alignment.

After beams 16 and 18 pass through prisms 26 and 28, they are directed toward lenses 30 and 32 for focusing the beams onto the stream of particles. As more clearly seen in FIG. 2, taken in conjunction with FIG. 1, lens 30 is tilted around a vertical axis so that the lens axis 31, through its optical center, forms an angle $\theta$ with the laser beam axis 16. It is preferred that the angle $\theta$ lie between zero and ten degrees for optimal purposes of the present invention, although this angle may vary widely, depending upon design factors and use of the cytometry device. When lens 30 is placed at such an angle, astigmatism is introduced into the beam as it passes through the lens. As a result, the optimal horizontal focal point 34 occurs closer to lens 30 than the optimal vertical focal spot 35. Furthermore, an elliptical beam spot 36 is generated in conjunction with vertical focal spot 35. For example, if lens 30 is tilted at an angle of 8.6 degrees around a vertical axis through its optical center, an elliptical focal spot of 13 micrometers vertical and 120 micrometers horizontal cross-section is formed as a result of the astigmatism introduced into the 6 mm diameter incident laser beam. Lens 30 is mounted within flow cytometry device 10 so as to be adjustable whereby the angle of tilt may be varied by the operator. Therefore, the amount of ellipticity may be adjusted by varying the angle of tilt of the lens. Moreover, if desired, fine focusing of lens 30 may be achieved by appropriate longitudinal adjustment mechanisms.

Figure 2:
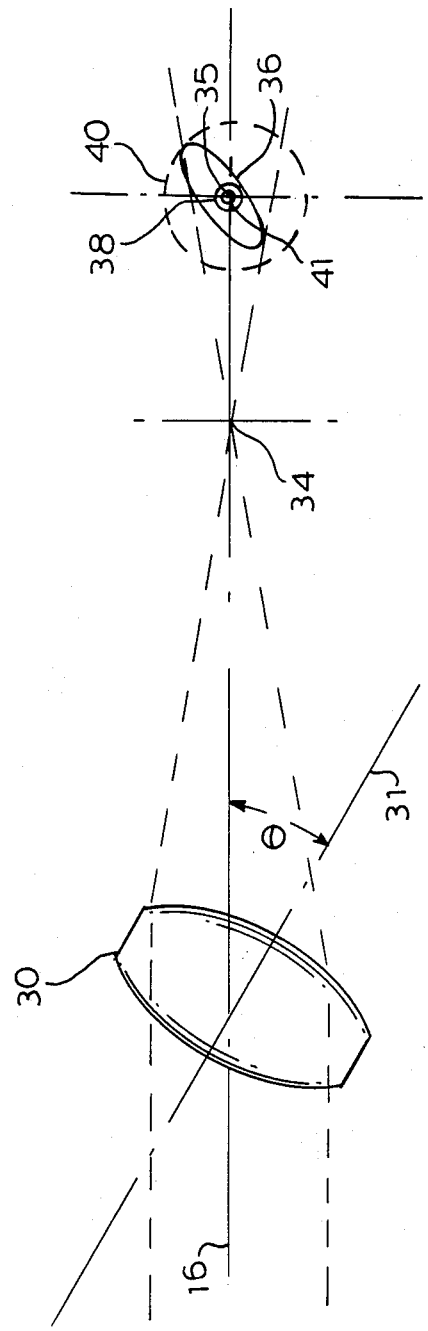
FIG. 2 is a schematic illustration, in top plan view, of the preferred orientation of the beam focusing lens of the present invention, showing, in enlarged form, its preferred orientation in the flow cytometry device.

While FIG. 2 depicts lens 30 in particularity and its effect on laser beam 16, it is understood that lens 32 functions equivalently to modify the effect of laser beam 18.

After passing through lenses 30 and 32, the laser beams are directed onto particle stream 38. A nozzle 40 (shown in photon in FIG. 2), incorporated within the flow cytometry device of the present invention, facilitates the flowing of particles 41 within fluid stream 38. The utilization of a nozzle of this type is well-known and is described, for example, in U.S. Pat. Nos. 3,826,364 and 4,110,604. As seen more clearly in FIG. 2, taken together with FIG. 1, nozzle 40 and lens 30 (and lens 32, although not shown in FIG. 2) are arranged in the present flow cytometry device so that stream 38 and particles 41 therein flow through optimal vertical beam focal spot 35, representing the shortest fluorescence pulse length. (In FIG. 2, stream 38 and particles 41 are flowing vertically into the plane of the paper.) Accordingly, and because of the width of the beam spot particularly in the horizontal plane, sensitivity to particle stream diameter is reduced.

In the flow cytometry device being described, the two laser beam-particle steam intersections are spaced approximately 250 micrometers apart. As seen more clearly in FIG. 1, laser beam 16 lies on the optical axis of the light-scatter channel and is used for scatter detection of particles. Thus, light beam 16 is the first light beam encountered by a particle flowing in stream 38 emerging from nozzle 40. Thereafter, beam 16 strikes the light-scatter obscuration bar 42 on the optical axis of the light-scatter channel. Scattered light, collected by the lens 44, passes through a first iris 45 which determines the maximum angle of scattered light collected. Following first iris 45 is a beam splitting mirror 46 which preferably reflects about ten percent of the incident light toward scatter detector 48, and transmits about ninety percent of the incident light onto a light absorber (not shown). A second iris 49 functions as a field stop to restrict the source of scattered light to the point of intersection of laser beam 16 and stream 38. After passing through filter 50, the scattered light is detected in detector 48. This detector functions electrically to assess the size of the particles flowing in the fluid stream according to well-known techniques.

In the embodiment of the present invention illustrated in FIG. 1, laser beam 18 is also directed at flowing stream 38, but is vertically displaced about 250 micrometers from laser beam 16, along the vertical axis of the stream. Light from beam 18 scattered by a particle is picked up by the scatter-channel optics, but preferably blocked from detector 48 by the dielectric filter 50 placed in the scatter channel. With respect to the fluorescence channel, illumination provided by the different wavelength operation of the lasers is available for sequential excitation of two different fluorochromes, such as fluorescein and rhodamine. As seen in FIG. 1, the two independent laser beams intersect stream 38 at points vertically spaced so that a particle crosses laser beam 16 first and then laser beam 18. Accordingly, two optical signals are generated for each particle. These signals are preferably spaced in time by the time required for the particle to travel from the first beam intersection point to the second beam intersection point. This time spacing permits the signals to be separately analyzed giving signals proportional to the fluorescence emissions of the particle when excited at the two different wavelengths. Fluorescence signals emitted from the particles are directed around obscuration bar 54 which blocks refracted light from the separated beams. The fluorescence signals are focused by lens 55 through a series of filters 56, 58 and 59 until they are picked up by detectors 60 and 61, respectively. These detectors may be low-noise photomultiplier tubes which devices convert fluorescence into electrical signals. A mirror 62 may be utilized, if desired, to bend one of the fluorescence signals for maximum utilization of space.

After particles 41 in stream 38 pass through the laser beams, the stream may be broken up into discrete drops so that they can be separated and collected in different receptacles. For example, drops with a fluorescent particle of desired luminescence, and which contain no other particles, may be deflected into a specific receptacle. Drops which contain other particles, such as fluorescent particles having different luminescence, and containing no fluorescent particles of the first luminescence may be deflected into a different receptacle. Furthermore, all drops which contain particles not desired to be sorted may be collected in still another receptacle. This technique of separating particles and drops is facilitated by the use of selectively charging the droplet stream and is described in greater detail in U.S. Pat. No. 3,826,364.

It is preferred, for purposes of the present invention that all of the lenses utilized herein be fabricated of fused silica for maximum transmission effects.

Thus, the present invention provides a flow cytometry device which provides optimum fluorescence pulse resolution by balancing illumination uniformity and laser beam intensity. In this regard, high resolution measurements of weakly fluorescent particles are possible. The expedient of elongating the laser beam focal waist by introducing astigmatism into the laser beam accounts for the desirable features of the present invention.

What is claimed is:

1. Flow cytometry apparatus comprising: means for flowing particles in a stream of fluid; a source of light adapted to direct a beam of light at said flowing particles; beam focusing lens means positioned in the optical path of said light beam so that an axis of said lens means, through its optical center, forms an angle with the axis of said beam of light for astigmatically providing an elliptical beam spot at the fluid stream to thereby elongate the focal spot of said beam; and means for detecting one or more parameters of the particles in said stream related to light from said beam striking said particles.

2. The apparatus of claim 1 wherein said means for flowing includes a nozzle for producing said stream of fluid with particles therein.

3. The apparatus of claim 1 wherein said lens means is positioned in said optical path at an angle around its vertical axis.

4. The apparatus of claim 3 wherein said lens means is a lens lying at an angle between, but not including, zero degrees and ten degrees around the vertical axis thereof.

5. The apparatus of claim 1 wherein said lens means is adjustably positioned in said optical path so that said angle may be varied.

6. The apparatus of claim 1 wherein said means for detecting includes a detector for light from said light beam scattered by striking particles in said fluid stream.

7. The apparatus of claim 1 wherein said means for detecting includes a detector for fluorescence generated by said particles as a result of said light beam striking same.

8. The apparatus of claim 1 wherein said light source is a laser.

9. An apparatus for detecting light parameters of particles flowing in a continuous stream comprising: a nozzle for producing a continuous stream of flowing particles; a laser adapted to direct a beam of light at a pre-selected wavelength of light; a beam focusing lens adjustably positioned in the optical path of said laser beam at an angle which can be varied around an axis through its optical center, said lens adapted to position the optimal horizontal focal point of said beam between the lens and the stream of flowing particles to astigmatically focus said laser beam onto said fluid stream to provide an elliptical beam spot at the fluid stream to thereby elongate the focal spot of said beam; a light detector for detecting light from said laser beam scattered by striking particles in said fluid stream; and a fluorescence detector to detect fluorescence generated by said particles as a result of said laser beam striking same.

10. The apparatus of claim 9 which further includes a second laser adapted to direct a beam of light at a second pre-selected wavelength of light, and a second beam focusing lens adjustably positioned in the optical path of said second laser beam at an angle which can be varied around an axis through its optical center, said second lens adapted to position the optimal horizontal focal point of said beam between the second lens and the stream of flowing particles to astigmatically focus said second laser beam onto said fluid stream to provide an elliptical beam spot at said fluid stream to thereby elongate the focal spot of said second beam.

11. The apparatus of claim 10 which further includes a second fluorescence detector for detecting fluorescence generated by said particles as a result of said second laser beam striking same.

12. The apparatus of claim 9 which further includes means for sorting particles after they pass through said light beam.

* * * * *